United States Patent [19]
Schmierer et al.

[11] Patent Number: 4,786,312
[45] Date of Patent: Nov. 22, 1988

[54] 1-PHENYLIMIDAZOLE COMPOUNDS AS GROWTH REGULATORS

[75] Inventors: Roland Schmierer, Todtenweis; Hilmar Mildenberger, Kelkheim; Helmut Büstell, Frankfurt am Main, all of Fed. Rep. of Germany

[73] Assignee: Hoechst Aktiengesellschaft, Frankfurt am Main, Fed. Rep. of Germany

[21] Appl. No.: 42,265

[22] Filed: Apr. 24, 1987

[30] Foreign Application Priority Data

Apr. 28, 1986 [DE] Fed. Rep. of Germany ....... 3614364

[51] Int. Cl.$^4$ .................... A01N 43/50; C07D 233/90
[52] U.S. Cl. ........................................ 71/92; 540/603; 544/139; 544/370; 546/210; 548/336; 548/343
[58] Field of Search .............. 548/336, 343; 546/210; 540/603; 544/139, 370; 514/397, 400, 326, 212, 234, 252; 71/92

[56] References Cited

U.S. PATENT DOCUMENTS 4,394,511  7/1983  Sawa et al. ........................ 548/343

*Primary Examiner*—Richard A. Schwartz
*Attorney, Agent, or Firm*—Curtis, Morris & Safford

[57] ABSTRACT

The new compounds of the formula I in which
R denotes substituted phenyl,
X denotes a radical of the formula —SH, or hydrogen,
Y denotes a radical of the formula $-CN$, $-\overset{O}{\underset{\|}{C}}-OR^4$, $-\overset{O}{\underset{\|}{C}}-SR^5$, $-\overset{S}{\underset{\|}{C}}-OR^5$, $-\overset{S}{\underset{\|}{C}}-SR^5$, $-\overset{O}{\underset{\|}{C}}-NR^6R^7$, $-\overset{S}{\underset{\|}{C}}-N(R^6)_2$, $-\overset{NOR^6}{\underset{\|}{C}}-NH_2$, $-\overset{O}{\underset{\|}{C}}-R^6$, $-\overset{NOR^8}{\underset{\|}{C}}-R^6$, $-CH_2-OR^8$, $-CF_3$, and other heterocyclic radicals, and the bisulfite adducts, acetals, ketals, thioacetals or thioketals derived from $-\overset{O}{\underset{\|}{C}}-R^6$, Z denotes O, S or N—R$^6$; m denotes 0, 1 or 2; n denotes 0, 1, 2, 3 or 4 and p denotes 2 or 3, and the salts and quaternization products which are acceptable for agricultural purposes have advantageous plant growth-regulating actions. Processes for the preparation thereof are also described.

6 Claims, No Drawings

1-PHENYLIMIDAZOLE COMPOUNDS AS GROWTH REGULATORS

DESCRIPTION

It is known that 1-phenylimidazole-5-carboxylic acid derivatives, see DE-A No. 3,217,094, have plant growth-regulating properties. Surprisingly, it has now been found that, when certain substituents on the phenyl ring are selected, the following imidazole compounds have advantageous plant growth-regulating actions in various crops.

The present invention relates to the novel compounds of the formula I in which
R denotes a radical of the formula X denotes a radical of the formula —SH, or —S(O)$_m$—R$^3$, or denotes hydrogen,
Y denotes a radical of the formula

—CN, —C(=O)—OR$^4$, —C(=O)—SR$^5$, —C(=S)—OR$^5$, —C(=S)—SR$^5$,

—C(=O)—NR$^6$R$^7$, —C(=S)—N(R$^6$)$_2$, —C(=NOR$^6$)—NH$_2$, —C(=O)—R$^6$, —C(=NOR$^8$)—R$^6$,

—CH$_2$—OR$^8$, —CF$_3$, ...

and the bisulfite adducts, acetals, ketals, thioacetals or thioketals which are derived from

—C(=O)—R$^6$,

Z denotes O, S or N—R$^6$,
m denotes 0, 1 or 2,
n denotes 0, 1, 2, 3 or 4
p denotes 2 or 3,
R$^1$, independently of one another denote (C$_1$-C$_4$)alkyl which may be halogenated, (C$_2$-C$_3$)alkenyl, halo(C$_2$-C$_3$)alkenyl, acetyl, hydroxy(C$_1$-C$_3$)alkyl, (C$_1$-C$_4$)alkoxy or halogen,
R$^2$, independently of one another, denote hydrogen, (C$_1$-C$_4$)alkyl, (C$_1$-C$_4$)alkoxy or halogen,
R$^3$ denotes (C$_1$-C$_4$)alkyl, (C$_2$-C$_4$)alkenyl, (C$_1$-C$_4$)alkoxycarbonyl (C$_1$-C$_2$)alkyl, phenyl or benzyl,
R$^4$ denotes hydrogen, (C$_1$-C$_{12}$)alkyl, (C$_1$-C$_{12}$)alkyl which is monosubstituted, disubstituted or trisubstituted by hydroxyl, halogen, (C$_1$-C$_6$)alkoxy, (C$_1$-C$_4$)alkoxy (C$_1$-C$_4$)alkoxy, (C$_1$-C$_4$)alkylthio, (C$_1$-C$_4$)alkylsulfinyl, (C$_1$-C$_4$)alkylsulfonyl, mono- or di-(C$_1$-C$_4$-alkyl)amino, cyano, aminocarbonyl, (C$_1$-C$_4$)alkanoyl, (C$_1$-C$_4$-alkoxy)carbonyl, cyclo-(C$_3$-C$_7$)alkyl, tri(C$_1$-C$_4$-alkyl)silyl, benzyloxy, benzyloxyethoxy, phenyl, or phenyl which is monosubstituted or polysubstituted by halogen or (C$_1$-C$_4$)alkyl, phenoxy and phenylthio which are both monosubstituted or polysubstituted by halogen or (C$_1$-C$_4$)alkyl, oxiranyl, tetrahydrofuryl, triazolyl, pyridinyl, imidazolyl, carboxyl, carboxylate having a cation which can be employed for agriculture, or the —O—N=C(CH$_3$)$_2$ radical, (C$_3$-C$_6$)alkenyl, halogenated (C$_3$-C$_6$)alkenyl, cyclo(C$_3$-C$_7$)alkyl which is unsubstituted or substituted by halogen or (C$_1$-C$_4$)alkyl, cyclo(C$_5$-C$_7$)alkenyl which is unsubstituted or substituted by halogen or (C$_1$-C$_4$)alkyl, (C$_3$-C$_6$)alkynyl, 1,2-epoxyprop-3-yl, phenyl, phenyl which is monosubstituted or disubstituted by halogen, nitro, cyano, (C$_1$-C$_4$)alkyl, (C$_1$-C$_4$-alkoxy)carbonyl or (C$_1$-C$_4$)alkoxy, (C$_1$-C$_4$-alkyl)carbonyl, phenylcarbonyl, it being possible for the phenyl ring to be substituted by halogen, nitro, cyano or (C$_1$-C$_4$)alkyl, a radical of the formula —N=C(R$^{10}$)$_2$, —NR$^6$R$^{11}$, or a cation which can be employed for agriculture,
R$^5$ denotes H, (C$_1$-C$_{12}$)alkyl, or (C$_1$-C$_{12}$)alkyl which is monosubstituted or disubstituted by (C$_1$-C$_4$)alkoxyethoxy, cyclo(C$_3$-C$_6$)alkyl, benzyloxy, phenyl, phenoxy, (C$_1$-C$_4$)alkylthio, (C$_1$-C$_4$-alkoxy)carbonyl, carboxyl or carboxylate having a cation which can be employed for agriculture, phenyl, or, in the case of —CS—OR$^5$, a cation which can be employed for agriculture, R$^6$, in each case independently of one another, denote hydrogen, (C$_1$-C$_6$)alkyl, phenyl, benzyl or methylphenyl, R$^7$ denotes hydrogen, (C$_1$-C$_{12}$)alkyl, or (C$_1$-C$_{12}$)alkyl which is monosubstituted or disubstituted by (C$_1$-C$_6$)alkoxy, (C$_1$-C$_4$)alkoxyethoxy, hydroxyl, halogen, cyclo(C$_3$-C$_6$)alkyl, benzyloxy, cyano, aminocarbonyl, carboxyl, (C$_1$-C$_4$-alkoxy)carbonyl, formyl, phenyl or phenoxy, phenyl, phenyl which is monosubstituted or disubstituted by halogen, nitro, cyano, (C$_1$-C$_4$)-alkyl or (C$_1$-C$_4$)alkoxy, (C$_3$-C$_6$)alkenyl, (C$_3$-C$_6$)cycloalkyl, or a radical of the formula —NR$^6$R$^{12}$, —OR$^6$, —NH—CONH$_2$, —NH—C-S—NH$_2$ or —SO$_2$R$^6$, or R$^6$ and R$^7$, together with the nitrogen atom to which they are bound, denote a saturated or unsaturated three- to seven-membered ring which is optionally fused to a benzene ring, contains up to three heteroatoms from the group comprising O, N and S, is unsubstituted or substituted by (C$_1$-C$_4$)alkyl or halogen and can contain a carbonyl group, R$^8$, in each case independently of one another, denote H, unsubstituted or phenyl-, halophenyl-, nitrophenyl-, cyanophenyl-, (C$_1$-C$_4$)alkylphenyl-, (C$_1$-C$_4$)alkoxyphenyl-, hydroxy-, cyano-, (C$_1$-C$_4$-alkoxy)carbonyl-, (C$_1$-C$_4$)alkylthio-, (C$_1$-C$_4$)alkoxy-, cyclo(C$_5$-C$_7$)alkyl- or benzyloxy-substituted (C$_1$-C$_{12}$)alkyl, cyclo(C$_5$-C$_8$)alkyl, (C$_3$-C$_6$)alkenyl, halo(C$_3$-C$_6$)alkenyl, (C$_3$-C$_6$)alkynyl, cyclo(C$_5$-C$_6$)alkenyl, (C$_1$-C$_6$-alkyl)carbonyl, halo(C$_1$-C$_6$-alkyl)carbonyl having 1 to 3 halogen atoms, (C$_1$-C$_6$-alkylamino)carbonyl, benzoyl, halobenzoyl or methylbenzoyl, R$^9$, in each case independently of one another, denote H, halogen, (C$_1$-C$_4$)alkyl, nitro or cyano, R$^{10}$, independently of one another, denote (C$_1$-C$_6$)alkyl, cyclo(C$_3$-C$_6$)alkyl, (C$_3$-C$_6$)alkenyl, phenyl or benzyl, or both radicals R$^{10}$, together with the carbon to which they are bound, denote cyclo(C$_5$-C$_7$)alkyl which is unsubstituted or substituted by methyl or halogen, R$^{11}$ denotes (C$_1$-C$_4$)alkyl, phenyl, (C$_1$-C$_6$-alkyl)carbonyl, benzyl, benzoyl, halobenzyl, halobenzoyl or methylbenzoyl, and R$^{12}$ denotes H, (C$_1$-C$_4$)alkyl, formyl, (C$_1$-C$_6$-alkyl)-carbonyl, benzoyl, halobenzoyl, methylbenzoyl or trihaloacetyl, and the salts and quaternization products thereof which are acceptable for agricultural purposes, with the proviso that only one radical R$^1$ may denote (C$_1$-C$_4$)alkyl. Salt formation or quaternization is carried out in the case of these compounds by addition of suitable compounds to the —S—R$^3$ group or to the basic nitrogen atom of the imidazole ring. Salt formation or quaternization is not possible when R$^4$ or R$^5$ denotes a cation, X represents —SH, or R$^4$ or R$^5$ contains a carboxylate group.

In the case where further basic nitrogen atoms are present in the substituents mentioned—in addition to the imidazole ring—multiple salt formation or quaternization is also possible.

All inorganic or organic acids which, as a result of their pKs value, are capable of salt formation are suitable for forming salts on the nitrogen, for example hydrohalic acids, nitric acid, sulfuric acid, phosphoric acid, phosphonic acid, sulfonic acid, haloacetic acids or oxalic acid.

Sulfonium salts (salt formation on sulfur) or quaternization products (salt formation on nitrogen) are taken to mean the products of the reaction with alkyl halides, alkylthioalkyl halides, alkoxyalkyl halides, in particular (C$_1$-C$_6$)alkyl halides, and optionally phenyl radical-substituted, in particular halogenated, phenacyl halides. The salts and quaternization products of the compounds of the formula I are prepared by generally conventional methods.

Suitable acetals, ketals and thioketals are, in particular, those of the formula —C(OR$^{13}$)$_2$R$^6$ or —C(SR$^{13}$)$_2$R$^6$ in which R$^{13}$ denotes (C$_1$-C$_2$)alkyl, or both radicals R$^{13}$ together denote a C$_2$- or C$_3$-alkylene chain which may be substituted by (C$_1$-C$_4$)alkyl, monohydroxy(C$_1$-C$_4$)alkyl, halo(C$_1$-C$_4$)alkyl having 1 to 3 halogen atoms, or phenyl.

Suitable heterocyclic rings for —NR$^6$R$^7$ are, in particular, piperidine, morpholine, 2,6-dimethylmorpholine, piperazine, imidazole, thiazole or benzimidazole. The alkyl, alkenyl and alkynyl radicals present in the definition of the general formula (1) can be either straight-chain or branched.

Halogen is taken to mean F, Cl, Br or I, in particular F, Cl or Br. In the case of R$^1$, fluorinated alkyl preferably denotes perfluorinated alkyl and very particularly preferably trifluoromethyl. Halogenated (C$_3$-C$_6$)alkenyl contains in particular, 1 to 3 bromine, chlorine or fluorine atoms.

Halophenyl, halobenzyl or halobenzoyl contain, in particular, 1 to 3 fluorine, chlorine or bromine atoms.

Trihaloacetyl is taken to mean, in particular, trichloroacetyl or trifluoroacetyl.

Suitable agriculturally applicable cations for R$^4$ and R$^5$ are metal cations, for example alkali metal or alkaline-earth metal cations, such as Na, K or Mg, or organic cations, such as organically substituted ammonium, organically substituted phosphonium, sulfonium or sulfoxonium, or other nitrogen cations.

Organically substituted ammonium denotes primary, secondary, tertiary, quaternary, aliphatic, aromatic or heteroaromatic ammonium which can contain 1 to 3 nitrogen atoms. The nitrogen atoms of the amine here can also be part of a cyclic system. Examples of such ammonium salts which may be mentioned are: mono-, di-, tri- and tetra[(C$_1$-C$_6$)alkyl]ammonium, such as isopropylammonium, butylammonium, stearylammonium and triethylammonium, mono-, di- or tri[(C$_1$-C$_4$)alkyl(-C$_1$-C$_4$)alkyl]ammonium, or mono-, di- or tri[(C$_1$-C$_6$)alkanol]ammonium, such as methoxyethylammonium, methoxypropylammonium, triethanolammonium or tripropanolammonium, or ammonium compounds with mixed radicals, such as tert.butyldiethanolammonium, triethylbenzylammonium, hydroxyethyltrimethylammonium or chloroethyltrimethylammonium; or allylammonium, diallylammonium, cyclohexylammonium, menthylammonium, aminoethylammonium, ethylenediammonium, benzhydrylammonium, pyrrolidinium, morpholinium, 3-piperidinium or piperazinium, or ammonium which is derived from an amino acid or an amino acid ester, such as NH$_3$—CH$_2$—COOCH$_3$.

Correspondingly, organically substituted phosphonium, organic sulfonium, or organic sulfoxonium contain aliphatic or arylaliphatic radicals.

Other nitrogen cations are, for example, hydrazonium, hydroxylammonium, guanidinium or aminoguanidinium, or the substitution products thereof.

Preferred compounds of the formula I

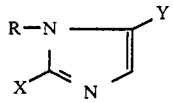

are those in whch
R denotes a radical of the formula

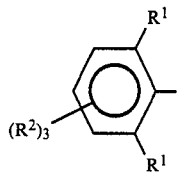

X denotes a radical of the formula —SH or

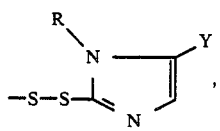

or hydrogen,
Y denotes a radical of the formula

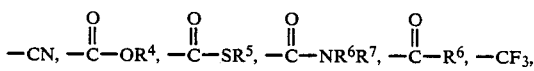

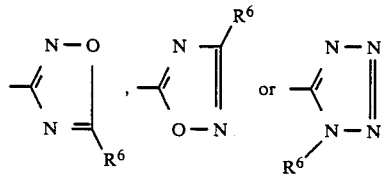

$R^1$, independently of one another, denote $(C_1-C_3)$alkyl which may be halogenated, $(C_2-C_3)$-alkenyl, halo($C_2-C_3$)alkenyl, acetyl, hydroxy$(C_1-C_3)$alkyl, $(C_1-C_4)$alkoxy or halogen, $R^2$, independently of one another, denote hydrogen $(C_1-C_4)$alkyl or halogen, $R^4$ denotes hydrogen, $(C_1-C_6)$alkyl, $(C_1-C_6)$alkyl which is monosubstituted, disubstituted or trisubstituted by hydroxyl, halogen, $(C_1-C_6)$alkoxy, $(C_1-C_4)$alkylthio, cyano, trimethylsilyl, benzyloxy or phenyl, $(C_3-C_6)$alkenyl, halogenated $(C_3-C_6)$alkenyl, cyclo$(C_3-C_7)$alkyl, halogenated $(C_3-C_6)$alkynyl, cyclo$(C_3-C_7)$alkyl, $(C_3-C_6)$alkynyl, phenyl or a radical of the formula —N=C$(R^{10})_2$ or

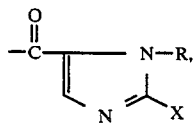

or a cation which can be employed in agriculture,
$R^5$ denotes H or $(C_1-C_6)$alkyl,
$R^6$ denotes hydrogen or $(C_1-C_6)$alkyl,
$R^7$ denotes hydrogen, $(C_1-C_6)$alkyl, $(C_1-C_6)$alkyl which is monosubstituted or disubstituted by $(C_1-C_2)$alkoxy, or denotes phenyl, $(C_3-C_6)$alkenyl, $(C_3-C_6$)cycloalkyl, or a radical of the formula —NR$^6$R$^{12}$ or —OR$^6$, $R^{10}$, independently of one another, denote $(C_1-C_4)$alkyl, and
$R^{12}$ denotes H or $(C_1-C_4)$alkyl,
and the salts and quaternization products which are acceptable for agricultural purposes, with the proviso that only one radical $R^1$ may denote $(C_1-C_4)$alkyl.

Particularly preferred compounds of the formula I

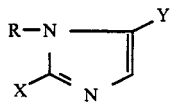

are those in which
R denotes a radical of the formula

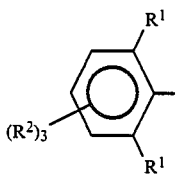

X denotes hydrogen,
Y denotes

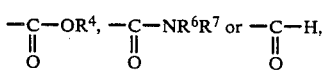

$R^1$, independently of one another, denote $(C_1-C_3)$alkyl, trifluoromethyl, vinyl, $(C_1-C_4)$alkoxy, fluorine or chlorine, $R^2$, independently of one another, denote hydrogen, methyl or chlorine, $R^4$ denotes hydrogen, $(C_1-C_6)$alkyl, $(C_1-C_6)$alkyl which is monosubstituted, disubstituted or trisubstituted by halogen or monosubstituted by trimethylsilyl, or denotes allyl, propargyl, a radical of the formula —N=C$(R^{10})_2$ or

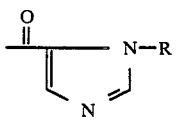

or a cation which can be employed in agriculture,
$R^6$ denotes hydrogen or $(C_1-C_6)$alkyl,
$R^7$ denotes hydrogen, $(C_1-C_6)$alkyl, $(C_1-C_6)$alkyl which is monosubstituted or disubstituted by methoxy or ethoxy, allyl, $(C_3-C_6)$cycloalkyl, or a radical of the formula —NR$^6$R$^{12}$ or —OR$^6$, $R^{10}$ denotes $(C_1-C_4)$alkyl, and
$R^{12}$ denotes hydrogen or methyl,
and the salts and quaternization products which are acceptable for agricultural purposes, with the proviso that only one radical $R^1$ may be $(C_1-C_3)$alkyl.

The invention furthermore relates to a process for the preparation of compounds of the formula I, and the salts or quaternization products thereof, where (a) a bisformyl ester of the formula IIa or IIb

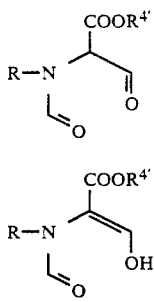
IIa

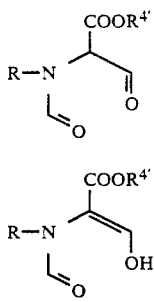
IIb where R⁴' denotes $(C_1-C_{12})$alkyl, (a₁) is cyclized with a $(C_1-C_3)$carboxamide, or (a₂) is reacted with an alkali metal thiocyanate or ammonium thiocyanate to form a 2-mercaptoimidazole derivative, and this, if desired, is desulfurized using nitric acid and sodium nitrite, and the resultant compounds are derivatized;

(b) an imidazole compound of the formula III

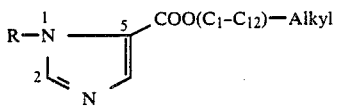

is metallized in the 2-position of the imidazole ring using a strong base, and subsequently reacted with a disulfide of the formula $R^3-S-S-R^3$ to form a compound of the formula I where $X=-S-R^3$ and $Y=COO(C_1-C_{12})$alkyl, and the resultant compounds are derivatized;

(c) an imidazole compound of the formula IV

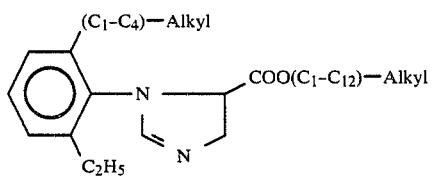

is oxidized on the ethyl group, a compound of the formula I where $R^1$=acetyl being obtained, and, if desired, the resultant compounds are derivatized; or (d) an imino compound of the formula Va or Vb $R-N=CH-COO(C_1-C_4)$-Alkyl  Va $R-N=CH-CF_3$  Vb is reacted with p-toluenesulfonyl methylisocyanide and, if desired, the resultant compounds of the formula I are derivatized.

The compounds in which X cannot represent hydrogen are derivatized in a known fashion, as described, for example, in Patent Application DE-A No. 3,537,290, either from 2-mercaptoimidazole (process version a₂) or by reacting the imidazole where X=H with disulfides in the presence of strong bases.

In derivatizing the substituents in the 5-position of the imidazole, the —COOR⁴' radical is modified in a known fashion, for example by saponification, esterification, transesterification, amidation, salt formation, reduction or oximation, as described, for example, in Patent Application DE-A Nos. 3,444,918 and 3,442,690, or salt formation or quaternization is carried out on the basic nitrogen atom of the imidazole ring.

In process (a₁), the carboxamide employed is preferably formamide. The carboxamide is preferably reacted in molar amounts in the presence of mineral acid at 50°–200° C., in particular 100°–170° C.

The bisformyl compounds of the formulae IIa and IIb can easily be obtained by known processes (German Offenlegungsschrift No. 3,217,094) from known anilines (for example 2-alkyl-6-trifluoromethylanilines, U.S. Pat. No. 4,503,276; 2-acetyl-, 2-alkenyl-, 2-hydroxyalkyl- and 6-alkylanilines, U.S. Pat. No. 4,456,471; 2-alkoxy-6-alkylanilines analogously to Gibson, Soc. 123, 1269; and 2-methyl-6-haloanilines analogous to P. Claus and W. Vycndilik, Tetrahedron Lett., 1968, 3610).

The imino compounds of the formulae Va and Vb can easily be prepared from the known anilines above and glyoxylates or trifluoroacetaldehyde. Cyclization to form the imidazoles of the formula I occurs in a known fashion (cf. V. A. van Lensen et al., J. Org. Chem., 42, 1153, (1977)) in good yield.

The phenylimidazole compounds IV are likewise known from the literature, see German Offenlegungsschrift No. 3,217,094. The ethyl group can be oxidized to the acetyl group using suitable oxidants (for example KMnO₄, pH 3–5). The acetyl group can be derivatized in a known fashion, for example by sodium borohydride reduction to the 1-hydroxyethyl group and by subsequent elimination of water to the vinyl group.

Compounds of the formula I where $R^1$=alkenyl can be converted into haloalkyl compounds in a known fashion, for example by addition of chlorine or bromine, and into haloalkenyl compounds by subsequent elimination.

The salts of the compounds of the formula (I) can be obtained by conventional salt-formation methods, for example by dissolving a compound of the formula (I) in a suitable organic solvent and adding the acid, and can be isolated in a known fashion, for example by filtering off, and purified, if appropriate, by washing with an inert organic solvent.

Typical growth-regulating effects can be achieved with the compounds according to the invention which—compared to the compounds known from DE-A No. 3,217,094—can be employed in various crops even at low dosages. They have a regulating effect on the plant's inherent metabolism and can thus be employed for influencing in a specific fashion plant substances and for simplifying harvesting, such as for initiating desiccation and inhibiting growth. In addition, they are suitable for general control and inhibition of undesired vegetative growth without at the same time killing the plants. Inhibition of vegetative growth plays an important part in many monocotyl and dicotyl crops since lodging can thereby be reduced or completely prevented. To be particularly emphasized is the growth-regulating activity of the compounds as growth inhibitors in cereals, corn, soybean, tobacco, cotton, field beans, rape, rice and grass, and their ability to increase the content of desired substances such as carbohydrates (for example sugar cane or millet crops) and protein in the case of crop plants. Finally, the compounds exhibit a very great improvement in fruit abscission, in particular in citrus fruits.

The agents can be used in conventional preparations as wettable powders, emulsifiable concentrates, sprayable solutions, dusting agents, dressing agents, dispersions, granules or microgranules.

In addition, the application further relates to plant-protection agents which are distinguished by an active content of at least one compound of the general formula (I).

In practical use, the compounds according to the invention can also be advantageously combined, if desired, with known growth regulators. Such known growth regulators are compounds of the formula

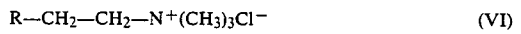

$$R-CH_2-CH_2-N^+(CH_3)_3Cl^- \qquad (VI)$$

in which R denotes OH or Cl (common name chlormequat for R=Cl), furthermore N,N-dimethylpiperidinium chloride (VII, mepiquat chloride), α-cyclopropyl-4-methoxy-α-(pyrimidin-5-yl)benzyl alcohol (VIII, ancymidol), (3aα,4β,4aα,6aα,7β, 7aα)-1-(4-chlorophenyl)-3a,4,4a,6a,7,7a-hexahydro-4,7-methano-1H-[1,2]diazeto-[3,4-f]benzotriazole (IX, tetcycla-cis), succinic acid mono(2,2-dimethylhydrazide) (X, diaminoazide), 6-hydroxy2H-pyridazin-3-one (XI, maleic hydrazide), 2-chloro-9-hydroxy-9H-fluorene-9-carboxylic acid (XII, chlorflurenol), 5'-(trifluoromethanesulfonamido)acet-2',4'-xylidide (XIII, mefluidide) and 2-chloroethylphosphonic acid (XIV, ethephone).

The growth regulating actions of the compounds of the formulae (VI) to (XIV) are described in Plant Growth Regulator Handbook of the Plant Growth Regulator Working Group, 2nd Edition, 1981.

In principle, the compounds of the formulae (VIII) and (VII) can also be replaced by comparable salts which, in place of the chloride ion, contain another conventional anion, such as bromide, nitrate or ½ sulfate.

Surprisingly, striking synergistic actions are shown when the compounds of the formula (I) are combined with the compounds of the formulae (VI) to (XIV). Thus, these combinations can be employed in even lower dosages than was to be expected from the action of the individual components for achieving the desired effects. The combinations can also be used to reduce natural vegetation so that the combinations can also be employed in landscape conservation. In addition, the combinations are highly suitable for general control and inhibition of undesired vegetative growth, such as side shoot formation, without killing the plants. The compounds of the formula (I) can also be combined advantageously with two different compounds of the formulae (VI) to (XIV).

The mixing ratios of the components of the general formula (I) to the compounds of the formulae (VI) to (XIV) can vary within broad limits, such as between 250:1 to 1:10. The choice of mixing ratios depends on the type of mixture components, on the state of development of the plants and on the degree of growth-regulating action desired. Mixing ratios from 10:1 to 1:10 are preferably selected.

The combinations can be present both as mixed formulations of the components, which are then used in a conventional fashion diluted with water; or they can be prepared as so-called tank mixes by common dilution of the separately formulated components with water; it is also possible to apply the components successively, i.e. to apply the components in individual formulations.

The compounds of the general formula (I) can also be combined with natural or vegetable hormones, such as auxins or cytokins.

The compounds of the general formula (I) according to the invention can be used, if appropriate, mixed with further active components, such as the compounds of the formulae VI to XII, in conventional preparations as wettable powders, emulsifiable concentrates, sprayable solutions, dusting agents, dressing agents, dispersions, granules or microgranules.

Wettable powders are preparations which are uniformly dispersible in water and which contain, besides the active compound(s) and, if appropriate, in addition to a diluent or inert material, wetting agents, such as polyoxyethylated fatty alcohols, alkyl- or alkylphenylsulfonates, and/or dispersing auxiliaries, such as sodium ligninsulfonate, sodium 2,2'-dinaphthylmethane-6,6'-disulfonate, sodium dibutylnaphthalenesulfonate or also sodium oleoylmethyl-taurinate. They are prepared in a conventional fashion, for example by grinding and mixing the components.

Emulsifiable concentrates can be prepared, for example, by dissolving the active compound(s) in an inert organic solvent, such as butanol, cyclohexanone, dimethylformamide, xylene or higher-boiling aromatics or aliphatic or cycloaliphatic hydrocarbons, with addition of one or more emulsifiers. In the case of liquid active compounds, the solvent component can also be omitted completely or partially. The following, for example, can be used as emulsifiers: calcium salts of alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide condensation products, alkyl polyglycol ethers, sorbitan fatty acid esters, polyoxyethylene sorbitan fatty acid esters or polyoxyethylene sorbitol esters.

Dusting agents can be obtained by grinding the active compound(s) with finely divided, solid substances, for example talcum, natural clays such as kaolin, bentonite, pyrophillite or diatomaceous earth. Granules can be prepared either by atomizing the active compound(s) onto adsorptive, granulated inert material or by applying active compound concentrates onto the surface of support materials, such as sand or kaolinites, or of granulated inert materials by means of binding agents, for example polyvinyl alcohol or sodium polyacrylate, or alternatively mineral oils. Suitable active compounds can also be prepared in the fashion conventional for the preparation of fertilizer granules—if desired as a mixture with fertilizers.

In wettable powders, the active compound concentration is about 10 to 90% by weight, and the remainder to 100% by weight comprises conventional formulation components. In the case of emulsifiable concentrates, the active compound concentration can be about 5 to 80% by weight. Dust-form formulations usually contain 0.05 to 20% by weight of active compound(s), and sprayable solutions about 2 to 20% by weight. In the case of granules, the active compound content depends partly on whether the active compound is liquid or solid and on which granulation auxiliaries, fillers etc. are used. In addition, the active compound formulations mentioned may contain the adhesives, wetting agents, dispersing agents, emulsifiers, penetrants, solvents, fillers or excipients which are conventional in each case.

Before use, the concentrates, present in commercially available form, are, if desired, diluted in a conventional fashion, for example using water in the case of wettable powders, emulsifiable concentrates, dispersions and, sometimes, also in the case of microgranules. Dust-form and granulated preparations and sprayable solutions are usually not further diluted with inert substances before use.

The amounts of the active compounds of the formula I applied can vary within broad limits. They are generally between 0.02 and 1.5 kg of active compound per hectare, preferably between 0.05 and 1 kg/ha.

CHEMICAL EXAMPLES

EXAMPLE 1

Ethyl 1-(2-ethyl-6-trifluoromethylphenyl)imidazole-5-carboxylate 1.3 g (3.9 mmol) of ethyl 2-(N-formyl-2-ethyl-6-trifluoromethylanilino)-3-hydroxyacrylate were heated for 4 hours at 150° C. with 20 ml of formamide and 5 ml of concentrated hydrochloric acid. After cooling, the mixture was extracted twice with diisopropyl ether, and the organic phase was washed with water, dried over sodium sulfate and evaporated. After chromatographic purification, 0.7 g (57% of theory) of ethyl 1-(2-ethyl-6-trifluoromethylphenyl)imidazole-5-carboxylate, a colorless oil, was obtained. The compound was identified by NMR spectroscopy.

The following examples can be prepared according to the process described above.

Where radicals other than $-COOCH_3$ or $COOC_2H_5$ represent Y in Tables 1 and 2, these were prepared from the appropriate esters by popular, generally known processes. The derivatives in which X does not represent hydrogen were prepared analogously to processes described in German Offenlegungsschrift No. 3,527,290.

TABLE 1

Imidazole compounds of the formula I in which one radical $R^1$ is $CF_3$.

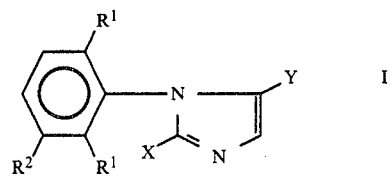

| Example No. | $R^1$ | $R^2$ | X | Y | b.p./m.p. [°C.] |
|---|---|---|---|---|---|
| 2 | $CH_3$ | H | H | $-COOH$ | |
| 3 | " | " | " | $-COOCH_3$ | |
| 4 | " | " | " | $-CN$ | |
| 5 | " | " | " | $-CONH_2$ | |
| 6 | " | " | " | $-C(=NOH)NH_2$ | |
| 7 | " | " | " | $-CHO$ | |
| 8 | " | " | " | $-CH(SC_2H_5)_2$ | |
| 9 | " | " | SH | $COOC_6H_{13}$ | |
| 10 | " | " | $SCH_3$ | $COOC_6H_{13}$ | |
| 11 | " | " | $S(=O)CH_3$ | $CON(CH_3)$phenyl | |
| 12 | " | " | $A(=O)_2CH_3$ | $CON\diagup O$ (morpholine) | |
| 13 | " | 3-Cl | H | $-COO^-.NH_4^+$ | |
| 14 | " | " | " | $-COO^-.N_3N^+-CH(-CH_3)_2$ | |
| 15 | " | " | " | $-COO.\tfrac{1}{2}Mg$ | |
| 16 | " | " | " | $-C(=O)NHOH$ | |
| 17 | " | 4-$CH_3$ | " | (oxime-type structure with $CH_3$) | |
| 18 | " | " | " | $-CONH-(CH_2)_2-OH$ | |
| 19 | $C_2H_5$ | H | " | $COOH$ | |
| 20 | " | " | " | $COONa$ | |
| 21 | " | " | " | $COOK$ | |
| 22 | " | " | " | $COO^-.HN(-CH_2CH_2-OH)_3$ | |
| 23 | " | " | " | $COO^-.H_2N^+$ (cyclohexyl) | |
| 24 | " | " | " | $COOH$ | (hydrochloride) |
| 25 | " | " | " | $COOCH_3$ | |
| 26 | " | " | " | $COOCH(-CH_3)_2$ | |
| 27 | " | " | " | $COO-N=C(CH_3)_2$ | |

TABLE 1-continued

Imidazole compounds of the formula I in which one radical $R^1$ is $CF_3$.

| Example No. | $R^1$ | $R^2$ | X | Y | b.p./m.p. [°C.] |
|---|---|---|---|---|---|
| 28 | " | " | " | COOCH$_2$CF$_3$ | |
| 29 | " | " | " | COOCH$_2$CH$_2$Cl | |
| 30 | " | " | " | COO(CH$_2$)$_3$—N(CH$_3$)$_2$ | |
| 31 | " | " | " | —CONH$_2$ | |
| 32 | " | " | " | —CONH—CH(OCH$_3$)$_2$ | |
| 33 | " | " | " | —CON(CH$_3$)CH$_2$—CH(OC$_2$H$_5$)$_2$ | |
| 34 | " | " | " | —CON(triazolyl) | |
| 35 | " | " | " | —CONH—cyclopropyl | |
| 36 | " | " | " | —CONH—phenyl | |
| 37 | " | " | " | —CONH—(4-Cl, 2-CH$_3$-phenyl) | |
| 38 | " | " | " | —COOCH$_2$—CH=CH$_2$ | |
| 39 | " | " | " | —COO—CH$_2$—C≡CH | |
| 40 | " | " | " | —C(=S)—NH$_2$ | |
| 41 | " | " | " | COSC$_2$H$_5$ | |
| 42 | " | " | SH | COOH | |
| 43 | " | " | S—CH$_2$—phenyl | " | |
| 44 | " | 4-Br | —S—phenyl | COOCH$_2$—COOCH$_3$ | |
| 45 | " | " | H | CH$_2$OH | |
| 46 | " | " | " | CH$_2$—O—COCH$_3$ | |
| 47 | " | " | " | CONH—N(CH$_3$)$_2$ | |
| 48 | " | " | " | CONH—O—benzyl | |
| 49 | " | " | " | CONH—OCH$_3$ | |
| 50 | " | " | " | —COO—C(=O)—[4-(2,6-(CF$_3$)(C$_2$H$_5$)-phenyl-amino)-pyrrolyl] | |
| 51 | " | " | " | —COO—phenyl | |
| 52 | " | " | " | —COO—CH$_2$CH$_2$—OCH$_3$ | |
| 53 | " | " | " | —CONH—CH$_2$—CN | |
| 54 | " | " | " | —COOCH$_2$—S—CH$_3$ | |
| 55 | " | " | " | —COOLi | |
| 56 | " | " | " | —CH=NOH | |
| 57 | " | " | " | —CH=NOCH$_3$ | |
| 58 | CH(CH$_3$)$_2$ | " | " | —COOH | |
| 59 | " | " | " | —COON=cyclopentylidene | |

TABLE 1-continued

Imidazole compounds of the formula I in which one radical $R^1$ is $CF_3$.

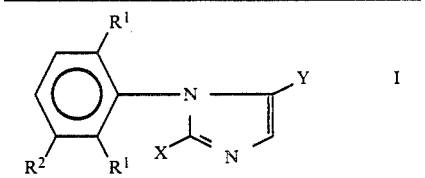

| Example No. | $R^1$ | $R^2$ | X | Y | b.p./m.p. [°C.] |
|---|---|---|---|---|---|
| 60 | " | " | —SH | —COOC$_{12}$H$_{25}$ | |
| 61 | " | " | —SCH$_2$COOCH$_3$ | —CONHC$_8$H$_{17}$ | |
| 62 | " | " | 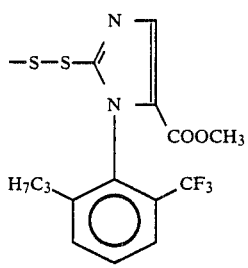 | —COOCH$_3$ | |

EXAMPLE 63

1-(2-Isopropenyl-6-methylphenyl)imidazole-5-carboxylic acid 8.0 g (0.03 mol) of ethyl 1-(2-isopropenyl-6-methylphenyl)imidazole-5-carboxylate (see Example 128) are heated for 2 hours at 80° C. with 100 ml of 2N sodium hydroxide solution. The mixture is cooled and acidified to pH 3 with concentrated hydrochloric acid, and the precipitate is filtered off under suction. 5.2 g (72% of theory) of 1(2-isopropenyl-6-methylphenyl)imidazole-5-carboxylic acid, a colorless solid of melting point 204° C. (decomposition), are obtained.

EXAMPLE 64

Ethyl 1-(2-(1,2-dibromoisopropyl-6-methylphenyl)imidazole-5-carboxylate 6.0 g (0.037 mol) of bromine in 100 ml of carbon tetrachloride are added dropwise to 10.0 g (0.037 mol) of ethyl 1-(2-isopropenyl-6-methylphenyl)imidazole-5-carboxylate at room temperature. After 1 hour, the mixture is poured into 200 ml of sodium carbonate solution, and the organic phase is separated off, washed with water and evaporated in vacuo. 14.3 g (89% of theory) of ethyl 1-(2-[1,2-dibromoisopropyl]-6-methylphenyl)imidazole-5-carboxylate, a solid of melting point 103°–105° C., are obtained.

$^1$H NMR (60 MHz, CDCl$_3$)δ = 1.07 (t, J = 7 Hz, 3H, —O—CH$_2$—CH$_3$), 1.83 (s, 3H, phenyl-CH$_3$), 1.91, 1.98 (2s, add. 3H=CBr-CH$_3$), 3.8–4.4 (sh, 4H, —OCH$_2$, —CBrH$_2$), 7.1–7.5 (m, 3H-phenyl-H), 7.7, 7.8 (2s, add. 1H, imidazole-H), 7.9 (s, 1H, imidazole-H) ppm.

EXAMPLE 65

Ethyl 1-(2-(1-bromoisoprop-1-enyl-6-methylphenyl)imidazole-5-carboxylate 8.3 g (0.019 mol) of ethyl 1-(2-(1,2-dibromoisopropyl-6-methylphenyl)imidazole-5-carboxylate (see Example 64) are refluxed for 3 hours in the presence of a sodium ethylate solution (prepared from 1.0 g of sodium (0.043 mol) and 50 ml of ethanol). The mixture is cooled and taken up in toluene/water, the organic phase is separated off, dried over sodium sulfate and evaporated. 6.3 g (95% of theory) of ethyl 1-(2-(1-bromoisoprop-1-enyl-6-methylphenyl)imidazole-5-carboxylate, a pale yellow solid of melting point 97°–99° C., are obtained.

EXAMPLE 66

Ethyl 1-(2-acetyl-6-ethylphenyl)imidazole-5-carboxylate*b

A solution of 27.3 g (0.13 mol) of potassium permanganate in 1000 ml of water is added dropwise to a solution of 21.8 g (0.080 mol) of ethyl 1-(2,6-diethylphenyl)imidazole-5-carboxylate and 121 g of magnesium nitrate in 300 ml of tert.-butanol at 20°–30° C. The mixture is stirred for a further 1 hour at 50° C., the manganese dioxide is filtered off under suction at this temperature, the mother liquor is extracted twice with toluene, the organic phase is dried (sodium sulfate) and evaporated, and the residue is chromatographed through a silica gel column (petroleum ether/ethyl acetate 9:1 to 1:1).

In addition to 11 g of educt, 8.6 g (75% of theory relative to reacted educt) of ethyl 1-(2-acetyl-6-ethylphenyl)imidazole-5-carboxylate, a pale yellow oil, are obtained.

$^1$H NMR (60 MHz, CDCl$_3$)δ = 1.07 (t, J = 7 Hz, 3H, phenyl-CH$_2$-CH$_3$), 1.2 (t, J = 7 Hz, 3H, —O—CH$_2$—CH$_3$), 2.23 (s, 3H, COCH$_3$), 2.31 (q, J = 7 Hz, 2H, phenyl-CH$_2$), 4.10 (q, J = 7 Hz, 2H, O—CH$_2$), 7.3–7.6 (sh, 4H, phenyl—H, imidazole—H), 7.83 (s, —H, imidazole—1H) ppm.

EXAMPLE 67

Ethyl 1-(2-ethyl-6-vinylphenyl)imidazole-5-carboxylate*b 10.6 g (0.04 mol) of ethyl 1-(2-ethyl-6-(1-hydroxy)ethylphenyl)imidazole-5-carboxylate (see Example 123) are heated for 5 hours at 100° C. with 30 g of polyphosphoric acid. After cooling, the mixture is taken up in methylene chloride/sodium hydroxide solution, the organic phase is separated off, evaporated and the residue is chromatographed through a silica gel column (petroleum ether/ethyl acetate 7:3).

5.9 g (56% of theory) of ethyl 1-(2-ethyl-6-vinylphenyl)imidazole-5-carboxylate, a colorless oil, are obtained.

$^1$H NMR (CDCl$_3$, 60 MHz) δ=1.07 (t, J=7 Hz, 3H, phenyl-CH$_2$CH$_3$), 1.20 (t, J=7 Hz, 3H, O—CH$_2$—CH$_3$), 2.27 (q, J=7 Hz, 2H, phenyl—CH$_2$), 4.03 (q, J=7 Hz, 2H, O—CH$_2$), 4.9-6.2 (m, 3H, —CH=CH$_2$), 7.1-7.4 (m, 3H, phenyl-H), 7.5, 7.9 (2s, je 1H, imidazole-H) ppm.

EXAMPLE 68

Ethyl 1-(2-butoxy-6-ethylphenyl)imidazole-5-carboxylate*b 13.5 g (0.07 mol) of 2-butoxy-6-ethylaniline are heated on a water separator with 11.8 g (0.099 mol) of ethyl glyoxylate in 100 ml of toluene until water formation is complete. The mixture is evaporated, the residue is dried in a high vacuum and taken up in 30 ml of dimethoxyethane, and the solution is added dropwise with 13.4 g (0.069 mol) of p-toluenesulfonylmethyl isocyanide to a suspension of 4.3 g (0.14 mol) of 80% strength sodium hydride (white oil) in 20 ml of dimethoxyethane at −20° C. When the gas evolution is complete, the mixture is hydrolyzed by adding water dropwise, the reaction products are extracted with methylene chloride, and the solvent is evaporated. The residue is taken up in 50 ml of ethanol, 20 g of potassium carbonate are added, and the mixture is stirred for 2 hours at 50° C. After evaporation, the residue is taken up in toluene/water, the organic phase is dried and evaporated, and the residue is chromatographed through a silica gel column (petroleum ether/ethyl acetate 8:2). 12.1 g (55% of theory relative to aniline employed) of ethyl 1-(2-butoxy-6-ethylphenyl)imidazole-5-carboxylate, a pale yellow oil, are obtained.

$^1$H NMR (CDCl$_3$, 60 MHz) δ=0.8-1.7 (sh, 13H), 2.33 (q, J=Hz, 2h, phenyl-CH$_2$), 3.83 (t, 2H, J=6 Hz, —O—CH$_2$—CH$_2$), 4.10 (q, J=7 Hz, 2H, —O—CH$_2$—CH$_3$), 6.7-7.3 (m, 3H, phenyl-H) 7.43, 7.83 (2s, per 1H, imidazole-H) ppm.

Further examples are collated in Table 2.

TABLE 2

Imidazole compounds

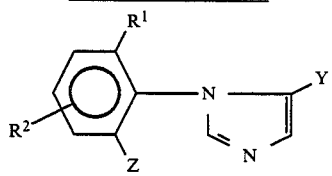

| Example No. | R$^1$ | R$^2$ | Z | Y | b.p./m.p. [°C.] |
|---|---|---|---|---|---|
| 69 | Cl | H | Cl | —COOH | 222-5 |
| 70 | " | " | " | —COOCH$_3$ | |
| 71 | " | " | " | —COOC$_2$H$_5$ | 123-4 |
| 72 | " | 4-Cl | " | —COOH | |
| 73 | " | " | " | —COOC$_2$H$_5$ | 124-7 |
| 74 | " | H | CH$_3$ | —COOH | 214-6 |
| 75 | " | " | " | —COOC$_2$H$_5$ | 135-40/0.1 torr |
| 76 | " | " | " | —CONH$_2$ | |
| 77 | " | " | C$_2$H$_5$ | —COOH | |
| 78 | " | " | " | —COOC$_2$H$_5$ | |
| 79 | " | " | " | —CONH$_2$ | |
| 80 | " | " | " | —COOK | >250˚ |
| 81 | " | 4-Cl | CH$_3$ | —COOH | 208-15 |
| 82 | " | " | " | —COOK | >100 decomp. |
| 83 | " | " | " | —COOCH$_3$ | |
| 84 | " | " | " | —COOC$_2$H$_5$ | 65-70 |
| 85 | " | " | " | —CONH$_2$ | |
| 86 | " | " | " | —CONHCH$_3$ | |
| 87 | " | " | " | —CON(CH$_3$)CH(CH$_3$)$_2$ | |
| 88 | " | 4-CH$_3$ | " | —COOH | 199-200 |
| 89 | " | " | " | —COOHN(—CH$_2$—CH$_2$OH)$_3$ | |
| 90 | " | " | " | —COOCH$_3$ | 106-110 |
| 91 | " | " | " | —COOC$_2$H$_5$ | 100-103 |
| 92 | " | " | " | —COO—n-C$_3$H$_7$ | 85-7 |
| 93 | " | " | " | —COO—i-C$_3$H$_7$ | 99-103 |
| 94 | " | " | " | —COO—CH$_2$—CF$_3$ | |
| 95 | " | " | " | —CONH$_2$ | 210-3 |
| 96 | " | " | " | —CONHCH$_3$ | 188-190 |
| 97 | " | " | " | —COON=C(CH$_3$)$_2$ | |
| 98 | " | " | " | —CONH—CH$_2$—CH(OCH$_3$)$_2$ | resin |
| 99 | " | " | " | —CON⟨ ⟩ | |
| 100 | " | " | " | —COSC$_2$H$_5$ | |
| 101 | " | 5-Cl | " | —COOH | |
| 102 | " | " | " | —COOC$_2$H$_5$ | |

TABLE 2-continued

Imidazole compounds

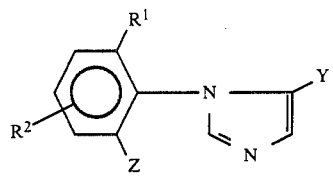

| Example No. | R¹ | R² | Z | Y | b.p./m.p. [°C.] |
|---|---|---|---|---|---|
| 103 | " | " | " | —CONH₂ | |
| 104 | F | H | " | —COOH | |
| 105 | " | " | C₂H₅ | —COOH | |
| 106 | " | " | " | —COOC₂H₅ | |
| 107 | OCH₃ | " | CH₃ | —COOC₂H₅ | |
| 108 | " | " | " | —CONH₂ | |
| 109 | " | " | OCH₃ | —COOC₂H₅ | |
| 110 | " | " | CH₃ | —COOC₂H₅ | |
| 111 | " | " | C₂H₅ | —COOH | |
| 112 | " | " | " | —COOCH₃ | |
| 113 | O—n-C₄H₉ | " | CH₃ | —COOH | |
| 114 | " | " | " | —COOCH₃ | |
| 115 | " | " | " | —COOC₂H₅ | |
| 116 | " | " | C₂H₅ | —COOH | |
| 117 | " | " | " | —COOK | |
| 118 | " | " | " | —COOCH₃ | |
| 119 | " | " | " | —COON=C(CH₃)₂ | |
| 120 | " | " | " | —CONH₂ | |
| 121 | " | " | " | —CF₃ | |
| 122 | CH₂—OH | " | " | —COOC₂H₅ | 94–100 |
| 123 | CH(OH)CH₃ | " | CH₃ | —COOH | |
| 124 | " | " | " | —COOC₂H₅ | |
| 125 | —CH=CH₂ | " | C₂H₅ | —COOH | |
| 126 | " | " | " | —COOCH₃ | |
| 127 | " | " | " | —CONH₂ | |
| 128 | —C(CH₃)=CH₂ | " | CH₃ | COOC₂H₅ | |
| 129 | " | " | " | —COOCH₃ | |
| 130 | " | " | " | —COOCH₂—CH₂—Cl | |
| 131 | " | " | " | —CONH₂ | |
| 132 | " | " | " | —CF₃ | |
| 133 | —C(=O)CH₃ | " | C₂H₅ | —COOH | |
| 134 | " | " | " | —COOCH₃ | |
| 135 | —C(CH₃)=CHBr | " | " | —COOH | |
| 136 | " | " | " | —COOCH₃ | |
| 137 | " | " | " | —CONH₂ | |

Biological Examples

Growth inhibition in cereals

In dish experiments in a greenhouse, young cereal plants (wheat, barley and rye) at the 3-leaf stage were sprayed with compounds according to the invention at various active compound concentrations (kg/ha) until dripping wet.

When the untreated control plants had reached a growth height of about 55 cm, the increase in growth in all plants was measured and the growth inhibition calculated in % of additional growth of the control plants. In addition, the phytotoxic action of the compounds was observed, 100% denoting growth cessation and 0% denoting growth corresponding to the untreated control plants. It was apparent that the compounds have very good growth-regulating properties. The results are collated in the following table.

TABLE 3

| Compound according to Ex. No. | Application conc. kg/ha | Growth inhibition (%) Wheat | Barley | Rye | Phytotoxic action |
|---|---|---|---|---|---|
| 128 | 1.25 | 14 | 21 | 10 | no |
|  | 0.62 | 10 | 17 | 7 | damage |
|  | 0.31 | 7 | 9 | 4 | |
| 81 | " | 22 | 34 | 14 | no |

TABLE 3-continued

| Compound according to Ex. No. | Application conc. kg/ha | Growth inhibition (%) Wheat | Barley | Rye | Phytotoxic action |
|---|---|---|---|---|---|
|  | " | 17 | 26 | 12 | damage |
|  | " | 10 | 15 | 9 | |
| 82 | " | 27 | 37 | 18 | no |
|  | " | 20 | 29 | 12 | damage |
|  | " | 16 | 21 | 9 | |
| 116 | " | 16 | 19 | 14 | no |
|  | " | 12 | 15 | 10 | damage |
|  | " | 9 | 11 | 7 | |
| 1 | " | 12 | 14 | 12 | no |
|  | " | 4 | 9 | 6 | damage |
|  | " | 0 | 3 | 3 | |

Growth inhibition in paddy rice

Rice plants were raised in pots in a greenhouse to the 3-leaf stage, and then treated with the compounds according to the invention. The substances were applied both by spraying and in the water. The additional growth in all plants was measured 3 weeks after treatment and the growth inhibition calculated in % of the additional growth of the control plants. In addition, a possible phytotoxic action of the compounds was watched for. The growth inhibition was determined as a percentage value, 100% denoting cessation of growth and 0% denoting growth corresponding to the untreated control plants. The results are collated in the following table.

TABLE 4

| Compound according to Ex. No. | Application conc. kg/ha | Growth inhibition (%) | Phytotoxic action |
|---|---|---|---|
| 75 | 1.25 | 21 | no damage |
|  | 0.62 | 13 |  |
|  | 0.31 | 7 |  |
| 109 | " | 20 | no damage |
|  | " | 14 |  |
|  | " | 8 |  |
| 63 | " | 19 | no damage |
|  | " | 15 |  |
|  | " | 9 |  |
| 128 | " | 22 | no damage |
|  | " | 15 |  |
|  | " | 11 |  |
| 81 | " | 19 | no damage |
|  | " | 15 |  |
|  | " | 9 |  |
| 116 | " | 18 | no damage |
|  | " | 12 |  |
|  | " | 7 |  |
| 68 | " | 17 | no damage |
|  | " | 12 |  |
|  | " | 9 |  |
| 1 | " | 14 | no damage |
|  | " | 8 |  |
|  | " | 4 |  |

We claim:

1. A compound of formula I

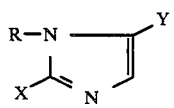
(I)

in which:

R is a radical of the formula

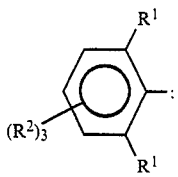

X is hydrogen;
Y is $$-\overset{O}{\underset{\|}{C}}-OR^4;$$

the substituents $R^1$ may be the same or different and each is $(C_1-C_4)$ alkyl which may be halogenated, $(C_2-C_3)$ alkenyl, halo$(C_2-C_3)$alkenyl, acetyl, hydroxy$(C_1-C_3)$alkyl, $(C_1-C_4)$alkoxy or halogne, provided that only one substituent $R^1$ may be $(C_1-C_4)$alkyl,
the substituents $R^2$ may be the same or different and each is hydrogen, $(C_1-C_4)$alkyl, $(C_1-C_4)$alkoxy or halogen;
$R^4$ is hydrogen or $(C_1-C_{12})$alkyl; or
a salt or quaternization product thereof which is acceptable for agricultural purposes.

2. A compound as claimed in claim 1 wherein:
the subsituents $R^1$ may be the same or different and each is $(C_1-C_3)$alkyl which may be halogenated, $(C_2-C_3)$alkenyl, halo$(C_2-C_3)$alkenyl, acetyl, hydroxy $(C_1-C_3)$alkyl $(C_1-C_4)$alkoxy or halogen provided that only one substituent $R^1$ may be $(C_1-C_3)$alkyl;
the substituents $R^2$ may be the same or different and each is hydrogen, $(C_1-C_4)$alkyl or halogen; and
$R^4$ is hydrogen or $(C_1-C_6)$alkyl.

3. A compound as claimed in claim 1 wherein:
the substituents $R^1$ may be the same or different and each is $(C_1-C_3)$alkyl, trifluoromethyl, vinyl, $(C_1-C_4)$alkoxy, fluorine or chlorine provided that only substituent $R^1$ may be $(C_1-C_3)$alkyl;
the substituents $R^2$ may be the same or different and is each hydrogen, methyl or chlorine; and
$R^4$ is hydrogen or $(C_1-C_6)$alkyl.

4. The compound as claimed in claim 1 which is 1-(2,4-dichloro-6-methylphenyl)-imidazole-5-carboxylic acid.

5. A plant growth-regulating agent comprising an effective amount of a compound of formula (I) as claimed in claim 1 and an inert carrier.

6. A process for regulating the growth of plants, wherein an effective amount of a compound of the formula (I) as claimed in claim 1 is applied to the plants or to the cultivated area.

* * * * *